US008507612B2

(12) United States Patent
Zhu et al.

(10) Patent No.: US 8,507,612 B2
(45) Date of Patent: Aug. 13, 2013

(54) AZIRIDINE CROSSLINKING AGENTS FOR ACRYLIC ADHESIVES

(75) Inventors: Peiwang Zhu, Woodbury, MN (US); Zhong Chen, Woodbury, MN (US); Babu N. Gaddam, Woodbury, MN (US); Larry R. Krepski, White Bear Lake, MN (US); Jingjing Ma, Cottage Grove, MN (US); David B. Olson, Marine on St. Croix, MN (US); Andrew Satrijo, St. Paul, MN (US); Dong-Wei Zhu, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 712 days.

(21) Appl. No.: 12/709,561

(22) Filed: Feb. 22, 2010

(65) Prior Publication Data
US 2010/0227969 A1 Sep. 9, 2010

Related U.S. Application Data

(60) Provisional application No. 61/158,485, filed on Mar. 9, 2009.

(51) Int. Cl.
*C08C 19/22* (2006.01)
*C08K 5/3412* (2006.01)
*C08F 8/30* (2006.01)
*C08J 3/24* (2006.01)
*C07D 203/16* (2006.01)

(52) U.S. Cl.
USPC ............ 525/329.9; 525/330.5; 525/375; 524/556; 524/560; 524/561; 548/954; 548/962; 548/964; 548/966; 548/969; 564/152; 564/153; 564/156

(58) Field of Classification Search
USPC ............ 524/556, 560, 561; 525/375, 329.9, 525/330.5; 548/954, 962, 964, 966, 969; 564/152, 153, 156
See application file for complete search history.

(56) References Cited

U.S. PATENT DOCUMENTS

| 2,964,426 | A | | 12/1960 | Ulrich |
| 3,507,837 | A | * | 4/1970 | Hidinger, Jr. ................. 528/336 |
| 3,691,140 | A | | 9/1972 | Silver |
| 4,166,152 | A | | 8/1979 | Baker et al. |
| 4,490,505 | A | * | 12/1984 | Pendergrass, Jr. ............ 524/591 |
| 4,636,432 | A | | 1/1987 | Shibano et al. |
| 4,645,789 | A | * | 2/1987 | Dabi ............................ 524/379 |
| 4,656,218 | A | | 4/1987 | Kinoshita |
| 5,045,569 | A | | 9/1991 | Delgado |
| 5,506,279 | A | | 4/1996 | Babu et al. |
| 5,902,836 | A | | 5/1999 | Bennett et al. |
| 6,879,718 | B2 | | 4/2005 | Hullender |
| 6,893,719 | B1 | | 5/2005 | Nakajima et al. |
| 7,714,076 | B2 | | 5/2010 | Krepski |
| 2003/0215630 | A1 | | 11/2003 | Melancon et al. |

FOREIGN PATENT DOCUMENTS

| DE | 4447615 | 7/1996 |
| EP | 0 530 729 | 3/1993 |
| JP | 01075577 | 3/1989 |
| JP | 02070780 | 5/1990 |
| JP | 02178379 | 7/1990 |
| JP | 03281586 | 12/1991 |
| JP | 04161477 | 6/1992 |
| JP | 04372682 | 12/1992 |
| JP | 07011211 | 1/1995 |
| JP | 07138542 | 5/1995 |
| JP | 07138544 | 5/1995 |
| WO | WO 79/01013 | 11/1979 |
| WO | WO 2008/046000 | 4/2008 |
| WO | WO 2009/120420 | 10/2009 |

OTHER PUBLICATIONS

Czech, Zbigniew, "New generation of crosslinking agents based on multifunctional methylaziridines," International Journal of Adhesion & Adhesives, vol. 27, (2007), pp. 49-58.*
PCT International Search Report, PCT/US2010/024222, Jun. 2010.

* cited by examiner

*Primary Examiner* — Roberto Rabago
(74) *Attorney, Agent, or Firm* — Kent S. Kokko

(57) ABSTRACT

A crosslinkable, pre-adhesive composition is described comprising an acid-functional (meth)acrylate copolymer and an aziridine crosslinking agent, which when crosslinked provides a pressure-sensitive adhesive and pressure-sensitive adhesive articles.

22 Claims, No Drawings

AZIRIDINE CROSSLINKING AGENTS FOR ACRYLIC ADHESIVES

CROSS REFERENCE TO RELATED APPLICATION

This application claims the benefit of U.S. Provisional Patent Application No. 61/158,485, filed Mar. 9, 2009, the disclosure of which is incorporated by reference herein in its entirety

TECHNICAL FIELD OF THE INVENTION

This invention relates to novel crosslinking agents and pressure sensitive acrylate adhesives and tape articles prepared therefrom. The adhesives are characterized by exhibiting an overall balance of adhesive and cohesive characteristics.

BACKGROUND OF THE INVENTION

Pressure sensitive tapes are virtually ubiquitous in the home and workplace. In its simplest configuration, a pressure sensitive tape comprises an adhesive and a backing, and the overall construction is tacky at the use temperature and adheres to a variety of substrates using only moderate pressure to form the bond. In this fashion, pressure sensitive tapes constitute a complete, self-contained bonding system.

According to the Pressure-Sensitive Tape Council, pressure-sensitive adhesives (PSAs) are known to possess properties including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These requirements are assessed generally by means of tests which are designed to individually measure tack, adhesion (peel strength), and cohesion (shear holding power), as noted in A. V. Pocius in *Adhesion and Adhesives Technology: An Introduction*, $2^{nd}$ Ed., Hanser Gardner Publication, Cincinnati, Ohio, 2002. These measurements taken together constitute the balance of properties often used to characterize a PSA.

With broadened use of pressure sensitive tapes over the years, performance requirements have become more demanding. Shear holding capability, for example, which originally was intended for applications supporting modest loads at room temperature, has now increased substantially for many applications in terms of operating temperature and load. So-called high performance pressure sensitive tapes are those capable of supporting loads at elevated temperatures for 10,000 minutes. Increased shear holding capability has generally been accomplished by crosslinking the PSA, although considerable care must be exercised so that high levels of tack and adhesion are retained in order to retain the aforementioned balance of properties.

There are two major crosslinking mechanisms for acrylic adhesives: free-radical copolymerization of multifunctional ethylenically unsaturated groups with the other monomers, and covalent or ionic crosslinking through the functional monomers, such as acrylic acid. Another method is the use of UV crosslinkers, such as copolymerizable benzophenones or post-added photocrosslinkers, such as multifunctional benzophenones and triazines. In the past, a variety of different materials have been used as crosslinking agents, e.g., polyfunctional acrylates, acetophenones, benzophenones, and triazines. The foregoing crosslinking agents, however, possess certain drawbacks which include one or more of the following: high volatility; incompatibility with certain polymer systems; generation of corrosive or toxic by-products; generation of undesirable color; requirement of a separate photoactive compound to initiate the crosslinking reaction; and high sensitivity to oxygen.

SUMMARY

The present invention provides a crosslinking agent of the formula:

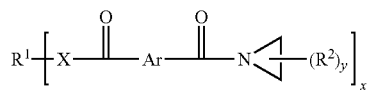

wherein
$R^1$ is a polyvalent organic group having a chain length of 2 to 250 atoms;
X is —O— or —NR$^3$—, where $R^3$ is H or a $C_1$-$C_4$ alkyl;
Ar is a divalent arylene group;
$R^2$ is H or $C_1$-$C_4$ alkyl;
x is 2 or 3, and y is 0, 1 or 2.

The present disclosure further provides a pre-adhesive composition comprising an acid-functional (meth)acrylate copolymer and the aziridine crosslinking agent. In one aspect, the disclosure provides a novel pre-adhesive syrup polymer composition comprising a) a first component acid-functional (meth)acrylate solute copolymer, b) a second component comprising at least one free-radically polymerizable solvent monomer, and c) the aziridine crosslinking agent. The pre-adhesive syrup polymer composition may be polymerized and cured to produce a pressure-sensitive adhesive.

In another embodiment the disclosure provides an adhesive emulsion comprising an aqueous emulsion of an acid-functional (meth)acrylate copolymer and the aziridine crosslinking agent, which may be coated and dried to form a pressure sensitive adhesive. In a related embodiment, the present disclosure provides an adhesive emulsion comprising an aqueous emulsion of the reaction product of the acid-functional (meth)acrylate copolymer, and the aziridine crosslinking agent which may be coated and dried to form a pressure sensitive adhesive.

The pressure-sensitive adhesives, the crosslinked compositions, of this disclosure provide the desired balance of tack, peel adhesion, and shear holding power, and further conform to the Dahlquist criteria; i.e. the modulus of the adhesive at the application temperature, typically room temperature, is less than $3 \times 10^6$ dynes/cm at a frequency of 1 Hz.

The use of the aziridine crosslinking agent affords a number of advantages as compared to the use of conventional crosslinking agents for (meth)acrylic adhesives. These advantages include, but are not limited to, decreased sensitivity of the crosslinkable composition to oxygen; the avoidance of evolution of any toxic or corrosive by-products or discoloration of the final product; and the capability to be used as a post-curing crosslinking additive. Furthermore, conventional bisamide-type crosslinking agents such as those aromatic bisamide crosslinking agents and acrylic adhesive prepared therefrom described in U.S. Pat. No. 6,893,719 (Melancon et al.) exhibit good shear properties and chemical and heat stability. However, the rigid nature of the crosslink deleteriously affects the low temperature performance and initial tack. Further, acrylic adhesive prepared using the aliphatic bisamide crosslinking agents of U.S. Pat. No. 6,893,719 have a very short pot life, limiting their utility.

The instant crosslinkers having a long chain group between the reactive aziridine groups can provide a more flexible crosslink between acrylate polymer chains. These flexible crosslinkers will tie linear polymers into networks, but the formed networks are not as rigid as those crosslinked with 1,1'-isophthaloyl-bis-1-methylaziridine, a conventional bisamide crosslinker. These new crosslinkers can provide a new set of polymer architecture and allow broader application temperature ranges. In addition, a flexible crosslinker can potentially crosslink a low molecular weight polymer so that it exhibits performance and properties like those of a high molecular weight linear polymer. Therefore low molecular weight adhesive polymers can be used to replace high MW equivalents. These low molecular weight adhesive polymers can be manufactured at high solids due to the low viscosity, and crosslinked to yield adhesives having the performance of high molecular weight adhesive polymers. This means higher manufacturing efficiency, lower manufacturing and materials cost, and more environmentally friendly products as lower amount of volatile organic chemicals (VOCs).

Because of the flexibility, flexible crosslinkers crosslink the polymer chains into a more homogenous network than a short, rigid crosslinker such as 1,1'-isophthaloyl-bis-1-methylaziridine (referred to hereinafter as "Bisamide"). They are also less susceptible to intra molecular crosslinking, which doesn't contribute to the overall cohesiveness of the adhesive. Therefore, at the same molar fraction, the new flexible crosslinker could lead to a stronger polymer network within an adhesive and better shear-holding capability than a short crosslinker. The feature of homogenous crosslinking may also be useful in optically clear adhesives, where optical clarity is desired.

In this application "pre-adhesive" refers to the composition comprising a acid-functional (meth)acrylate copolymer and the aziridine crosslinking agent which is crosslinked to form a pressure sensitive adhesive. "Syrup polymer" refers to a solution of a solute polymer in one or more solvent monomers, the solution having a viscosity of from 500 to 10,000 cPs (centipoise) at 22° C. "Solution polymer" refers to a solution of a solute polymer in one or more organic solvents. (Meth)acrylic is inclusive of both methacrylic and acrylic.

For environmental reasons, there is a desire to move away from the use of volatile organic solvents (VOC's) in coating processes, and towards more environmentally friendly water-based materials, so the present invention provides a waterborne adhesive comprising an aqueous emulsion of an acid-functional (meth)acrylate copolymer and the aziridine crosslinking agent. Waterborne systems are desirable for cost, environmental, safety, and regulatory reasons. The aqueous system may be readily coated, and provides a pressure-sensitive adhesive when dried. In other embodiments, the adhesive copolymer may be prepared by syrup polymerization methods, comprising a solution of a solute polymer in one or more solvent monomers, which may be coated and polymerized without the use of volatile organic solvents.

DETAILED DESCRIPTION

The present disclosure provides a novel aziridine crosslinking agent of the formula:

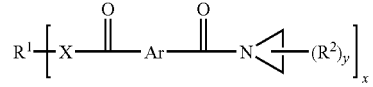

wherein
$R^1$ is a polyvalent organic group having a chain length of 2 to 250 atoms;
X is —O— or —NR$^3$—, where $R^3$ is H or a $C_1$-$C_4$ alkyl;
Ar is a divalent arylene group;
$R^2$ is H or $C_1$-$C_4$ alkyl;
x is 2 or 3, and y is 0, 1 or 2.

In one embodiment, the $R^1$ group is a polyvalent alkylene of 2 to 250 carbon atoms, preferably 10 to 100 carbon atoms. The alkylene chain may be linear or branched, and cyclic or acyclic. The alkylene chain may optionally be interrupted with one or more ether oxygen atoms, ester groups, amide groups or urea group. In one preferred embodiment, the $R^1$ group is a divalent alkylene of the formula —$C_aH_{2a+2}$—, where "a" is 2 to 250, preferably 10 to 150.

In another embodiments, $R^1$ is a poly(alkylene oxide) having a chain length of 2 to 250 atoms. Such poly(alkylene oxide) compounds are hydrophilic and suitable for use in aqueous emulsion and water-based adhesives. Such poly(alkylene oxide) group may be of the formula —(CH($R^4$)—$CH_2$—O)$_m$—CH($R^4$)—$CH_2$—O—, wherein $R^4$ is a H or a $C_1$ to $C_4$ alkyl group, and m is from 2 to 100, preferably 5 to 20.

Aziridine crosslinking agents of Formula I may be prepared by the condensation of an α,ω diol or diamine with a bis-acyl aryl compound followed by reaction with an aziridine compound as in the following scheme.

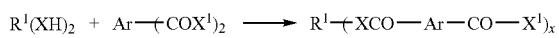

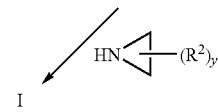

wherein
$R^1$ is a polyvalent organic group having a chain length of 2 to 250 atoms;
X is —O— or —NR$^3$—, where $R^3$ is H or $CH_3$;
$X^1$ is a hydroxyl, ester, or halide;
Ar is a di- or trivalent arylene group;
$R^2$ is H or $C_1$-$C_4$ alkyl;
x is 2 or 3, and y is 0, 1 or 2. In the second step, if $X^1$ is a hydroxyl, it should first be converted to a halide or ester prior to reaction with the aziridine compound.

In some embodiments, in the first step a large excess of the diacid (or functional equivalent thereof such as acyl halide or ester) is used relative to the diol (or diamine). The excess diacid (or functional equivalent thereof) may be subsequently recovered and reused for later preparations.

In certain preferred embodiments, the bisacyl aryl compound is an aryl anhydride. It has been found that such as aryl ortho anhydrides are more efficient starting materials in the preparation of the crosslinking agents of Formula I. Such anhydrides may be reacted with a stoichiometric equivalent of the long chain diol or diamine. Useful anhydrides include phthalic anhydride, 4-methylphthalic anhydride, and 1,2-, 2,3- and 1,8-naphthacene anhydride, 1,2-, 2,3- and 1,9-anthrathacene anhydride, 1,2-, 3,4- and 9,10-phenanthrene anhydride, and 4,5- and 5,6-benzonapthene anhydride.

Suitable long chain diols include poly(oxyalkylene)glycols in which the alkylene group contains from 2 to 250 carbon atoms, preferably from 4 to 50 carbon atoms and more preferably from 6 to 10 carbon atoms. Among these compounds are poly(alkylene oxide) glycols and polyether glycols such as poly(oxyethylene)glycols having molecular weights of about 200, 600, 1000, and 2000, poly(oxypropylene)glycols, having molecular weights of about 425 and 1800, poly(oxytetramethylene)glycols, poly(oxypentamethylene)glycol, poly(oxyhexamethylene)glycols, poly(oxyheptamethylene)glycols, poly(oxyoctamethylene)glycols, poly(oxynonamethylene)glycols, poly(1,2-butylene oxide)glycol, random or block copolymers thereof, for example, glycols derived from ethylene oxide and 1,2-propylene oxide and poly-formulas prepared by reacting formaldehyde with glycols, such as pentamethylene glycol, or mixtures of glycols, such as a mixture of tetramethylene and pentamethylene glycols. Also included are poly(lactone)glycols, e.g., poly (caprolactone)glycol; poly(oxyalkylenecarbonate)glycols, e.g., poly(oxyethylenecarbonate)glycol; and glycols containing a hydrocarbon main chain, e.g., hydroxy-terminated polybutadiene. The corresponding diamines may also be used.

In certain preferred embodiments, the diol or diamine is of the formula:

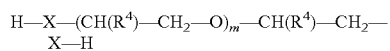

Wherein
X is —O— or —NR$^3$—, where R$^3$ is H or CH$_3$;
R$^4$ is a H or a C$_1$ to C$_4$ alkyl group, and
m is from 2 to 100, preferably 5 to 30. In one embodiment, the poly(alkylene oxide) group is a poly(ethylene oxide) (co) polymer. In another embodiment, the poly(alkylene oxide) group is a poly(ethylene oxide-co-propylene oxide) copolymer. Such copolymers may be block copolymers, random copolymers, or gradient copolymers.

Useful aryl diacyl compounds include those having two carboxylic acid groups (or derivatives thereof such as ester or acid halide) and an arylene ring. The term "arylene" refers to divalent aromatic carbocyclic radicals having one to six aromatic rings, such as phenylene or multiple fused rings, such as naphthylene or anthrylene, or combinations thereof. Examples of suitable arylene diacids include benzene-1,3-dicarboxylic acid, benzene-1,4-dicarboxylic acid, naphthalene-2,7-dicarboxylic acid, naphthalene-2,6-dicarboxylic acid, naphthalene-1,4-dicarboxylic acid, naphthalene-1,5-dicarboxylic acid, acenaphthene-dicarboxylic acid, phenanthen-3,8-dicarboxylic acid, 5,6-dihydrophenathren-3,8-dicarboxylic acid, fluoren-2,7-dicarboxylic acid, anthracene-9,10-dicarboxylic acid, perylene-3,9-dicarboxylic acid, perylene-3,10-dicarboxylic acid, and the like. The arylene groups may be further substituted with one or more C$_{1-10}$ alkyl or C$_{6-20}$ aryl groups. A preferred aryl diacyl compound is isophthalic anhydride.

A preferred crosslinking agent is of the formula:

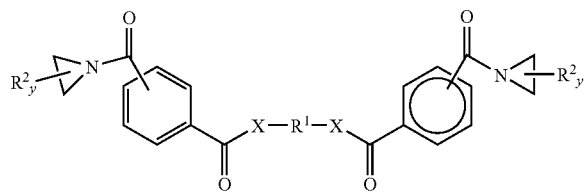

where
R$^1$ is a polyvalent organic group having a chain length of 2 to 250 atoms;
X is —O— or —NR$^3$—, where R$^3$ is H or CH$_3$;
R$^2$ is H or C$_1$-C$_4$ alkyl;
and y is 0, 1 or 2. The above compound may be derived from a 1,2-, 1,3-, or 1,4-bisacyl compound. Preferably the crosslinking agent is derived from isophthalic anhydride.

In another embodiment, the R$^1$ group of Formula I is derived from the reaction between an excess of an aryl bisamide compound and an aromatic or aliphatic diacid compound as shown in the following scheme. The aryl bisamide compounds shown in the scheme may be prepared as described in U.S. Pat. No. 6,879,718 (Melancon et al.), incorporated herein be reference.

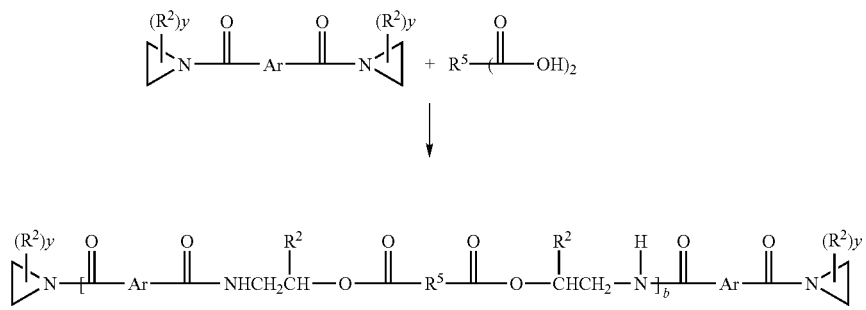

wherein
Ar is a divalent arylene group;
R$^2$ is H or C$_1$-C$_4$ alkyl;
b is at least 1, and generally 1-6;
y is 0, 1 or 2;
R$^5$ is selected from divalent C$_1$-C$_{20}$ alkylene, arylene, alkyarylane or poly(alkylene oxide). With respect to the above reaction scheme, it will be understood that the R$^2$ group may be on the carbon depicted, or on the carbon adjacent to the amide nitrogen atom, depending on the ring opening of the aziridine.

Thus, with respect to Formula I, $R^1$ may be selected as

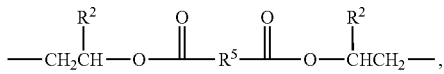

where $R^2$ and $R^5$ are as previously defined.

The present disclosure provides a pre-adhesive composition comprising an acid-functional (meth)acrylate copolymer and an aziridine crosslinking agent, which when crosslinked, provides a pressure-sensitive adhesive and pressure-sensitive adhesive articles.

The (meth)acrylate ester monomer useful in preparing the acid functional (meth)acrylate adhesive copolymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 1-dodecanol, 1-tridecanol, 1-tetradecanol, citronellol, dihydrocitronellol, 2-propylheptanol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable sources, such as 2-octanol, citronellol, and dihydrocitronellol.

The (meth)acrylate ester monomer is present in an amount of 85 to 99 parts by weight based on 100 parts total monomer content used to prepare the polymer. Preferably the (meth)acrylate ester monomer is present in an amount of 90 to 95 parts by weight based on 100 parts total monomer content.

The polymer further comprises an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl(meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 1 to 15 parts by weight, preferably 1 to 10 parts by weight, based on 100 parts by weight total monomer.

The polar monomers useful in preparing the copolymer are both somewhat oil soluble and water soluble, resulting in a distribution of the polar monomer between the aqueous and oil phases in an emulsion polymerization. Useful polar monomers are non-acid functional.

Representative examples of suitable polar monomers include but are not limited to 2-hydroxyethyl(meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl(meth)acrylate, 2-ethoxyethyl(meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 1 to 5 parts by weight, based on 100 parts by weight total monomer.

When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. Such vinyl monomers are generally used at 0 to 5 parts by weight, preferably 1 to 5 parts by weight, based on 100 parts by weight total monomer.

In order to increase cohesive strength of the coated adhesive composition, a multifunctional (meth)acrylate may be incorporated into the blend of polymerizable monomers. Multifunctional acrylates are particularly useful for emulsion or syrup polymerization. Examples of useful multifunctional (meth)acrylate include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition. Typically, the multifunctional (meth)acrylate is present in amounts less than 5 parts based on total dry weight of adhesive composition. More specifically, the multifunctional (meth)acrylate may be present in amounts from 0.01 parts to 1 part based on 100 parts total monomers of the adhesive composition.

The adhesive composition further comprises an aziridine crosslinking agent, in addition to the (meth)acrylate copolymer. The aziridine crosslinking agent is generally added in amounts of 0.005 to 5.0 parts by weight of an aziridine crosslinking agent, relative to 100 parts of the copolymer.

It is believed that the aziridine group reacts with the pendent acid functional groups of the acid functional (meth)acrylate copolymer to form a carboxyethyleneamino linkage. In one embodiment, the intermediate may be of the following structure, with the optional monomer units and unreacted (free) acid functional monomer units not shown. Subsequently, an acid group from an adjacent polymer chain may react with a second aziridinyl group forming the crosslink shown.

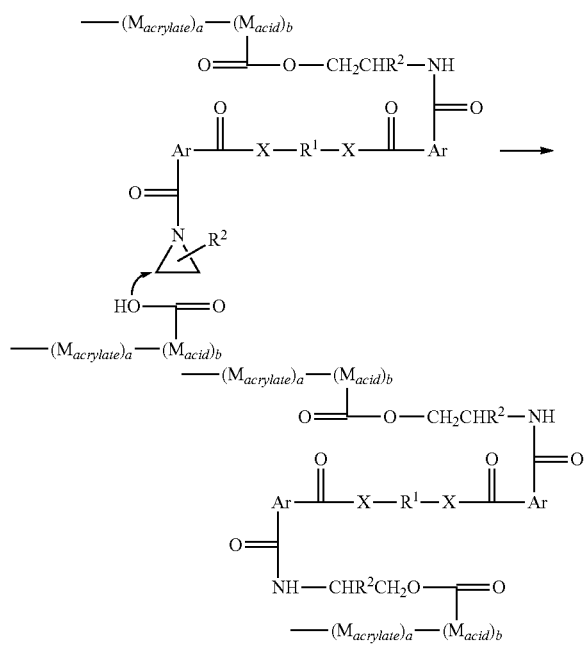

where $M_{acrylate}$ represents polymerized monomer units derived from (meth)acrylate monomers, $M_{acid}$ represents polymerized monomer units derived from acid functional monomers, a and b are integers of at least one, such that a+b is polymeric, $R^1$ is a polyvalent organic group having a chain length of 2 to 250 atoms;

X is —O— or —$NR^3$—, where $R^3$ is H or a $C_1$-$C_4$ alkyl;

Ar is a divalent arylene group;

$R^2$ is H or $C_1$-$C_4$ alkyl. With respect to the above reaction scheme, it will be understood that ring opening of the aziridine ring may occur at either of the aziridine ring carbon atoms.

The polymers herein can be prepared by any conventional free radical polymerization method, including solution, radiation, bulk, dispersion, emulsion, and suspension processes. The (meth)acrylate polymers may be prepared via suspension polymerizations as disclosed in U.S. Pat. Nos. 3,691,140 (Silver); 4,166,152 (Baker et al.); 4,636,432 (Shibano et al.); 4,656,218 (Kinoshita); and 5,045,569 (Delgado). Each describes adhesive compositions, and the descriptions of polymerization processes are incorporated herein by reference.

Water-soluble and oil-soluble initiators useful in preparing the (meth)acrylate adhesive polymers used in the present invention are initiators that, on exposure to heat, generate free-radicals which initiate (co)polymerization of the monomer mixture. Water-soluble initiators are preferred for preparing the (meth)acrylate polymers by emulsion polymerization.

Suitable water-soluble initiators include but are not limited to those selected from the group consisting of potassium persulfate, ammonium persulfate, sodium persulfate, and mixtures thereof; oxidation-reduction initiators such as the reaction product of the above-mentioned persulfates and reducing agents such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include but are not limited to those selected from the group consisting of azo compounds such as VAZO™ 64 (2,2'-azobis(isobutyronitrile)), VAZO™ 67 (2,2'azobis(2-methylbutyronitrile)), and VAZO™ 52 (2,2'-azobis(2,4-dimethylpentanenitrile)), available from E.I. du Pont de Nemours Co., peroxides such as benzoyl peroxide and lauroyl peroxide, and mixtures thereof. The preferred oil-soluble thermal initiator is 2,2'-azobis(2,4-dimethylpentanenitrile. When used, initiators may comprise from about 0.05 to about 1 part by weight, preferably about 0.1 to about 0.5 part by weight based on 100 parts by weight of monomer components in the pressure sensitive adhesive.

The copolymerizable monomer mixture may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The emulsion mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

Polymerization via emulsion techniques may require the presence of an emulsifier (which may also be called an emulsifying agent or a surfactant). Useful emulsifiers for the present invention include those selected from the group consisting of anionic surfactants, cationic surfactants, nonionic surfactants, and mixtures thereof.

Preferably, the emulsion polymerization of this invention is carried out in the presence of anionic surfactant(s). A useful range of emulsifier concentration is from about 0.5 to about 8 weight percent, preferably from about 1 to about 5 weight percent, based on the total weight of all monomers of the emulsion pressure sensitive adhesive. Generally the pH of the resulting emulsions is greater than 7.

The pressure sensitive adhesives may also contain one or more conventional additives. Preferred additives include tackifiers, plasticizers, dyes, antioxidants, and UV stabilizers. Such additives can be used if they do not affect the superior properties of the pressure sensitive adhesives.

If tackifiers are used, then up to about 40% by weight, preferably less than 30% by weight, and more preferably less than 5% by weight based on the dry weight of the total adhesive polymer would be suitable.

However, for some substrates, particularly low surface energy substrates, the acrylate copolymers may be highly tackified. Low energy substrates are those having a surface energy of less than 40 millinewtons per meter (mN/m), e.g., less than 35 mN/m. Exemplary low surface energy materials include polyolefins such as polypropylene and polyethylene (e.g., high density polyethylene).

In such compositions for low energy substrates the adhesives may comprise 40 to 60% by weight (wt. %) total tackifier content, based on the total weight of all tackifiers divided by the total weight of the acrylic copolymer and all tackifiers.

Suitable tackifiers for use with (meth)acrylate polymer composition include rosin acids, rosin esters, terpene phenolic resins, hydrocarbon resins, and cumarone indene resins. The type and amount of tackifier can affect properties such as contactability, bonding range, bond strength, heat resistance and specific adhesion.

Commercially available tackifiers for the adhesive compolymers include Foral™ 85LB from Hercules, Escorez™

2520 Liquid aliphatic/aromatic modified tackifing resin, available from Exxon Chemical Co., Houston, Tex., Escorez™ 2101 aliphatic/aromatic hydrocarbon tackifying resin, available from Exxon Chemical Co., Wingtack Plus™ C5 aliphatic aromatically modified tackifying resin, Wingtack Extra™ $C_5$ aliphatic aromatically modified tackifying resin, and Wingtack 10™ Liquid $C_5$ aliphatic tackifying resin, available from Goodyear Chemical, Akron, Ohio, Foral 85™ rosin esters, from Hercules, Inc., Piccotex™ LC-55wk aromatic resins, and Piccotac™ 95 aliphatic resins, both from Hercules, Inc., Piccolyte™ A-115 and Zonarez™ B-100 terpene resins both from Arizona Chemical Co., ECR-180™ hydrocarbon resins, from Exxon Chemical Co., and SP 553™ a terpene phenolic tackifier resin, from Schenectady International.

Commercially available tackifiers that are suitable for an aqueous dispersion include Tacolyn™ 1070, 5001 and 5002 (aqueous, 55% solids synthetic resin dispersions based on low molecular weight thermoplastic resins, available from Hercules Inc.), SE1055™ (an aqueous dispersion of a rosin ester, available from Hercules Inc.), Escorez™ 9271 (an aliphatic hydrocarbon resin emulsion, available from Exxon), Dermulsene™ 82, Dermulsene™ 92, Dermulsene™ DT or Dermulsene™ DT50 (aqueous dispersions of modified terpene phenolic resins, available from DRT) and Aquatak™ 4188 (a modified rosin ester, available from Arizona Chemical Company).

The adhesive composition of the present invention may contain a plasticizer, if desired. The plasticizer softens the adhesive, and as a result, the substrate is more easily wetted by the adhesive. Further, the use of a plasticizer may improve the adhesive properties, including peel and shear. The plasticizer may be hydrophobic oils, hydrophilic or a combination thereof. The plasticizer can be added in an amount ranging from about 0.1 to about 20 weight percent of the adhesive composition and preferably from about 0.5 to about 10 weight percent.

Useful plasticizers are compatible with the acrylic pressure sensitive adhesive, such that once the plasticizer is mixed into the acrylic pressure sensitive adhesive, the plasticizer does not phase separate from the pressure sensitive adhesive. By "phase separation" or "phase separate," it is meant that by differential scanning calorimetry (DSC) no detectable thermal transition, such as a melting or glass transition temperature can be found for the pure plasticizer in the plasticized adhesive composition. Some migration of the plasticizer from or throughout the plasticized adhesive can be tolerated, such as minor separation due to composition equilibrium or temperature influences, but the plasticizer does not migrate to the extent that phase separation occurs between the adhesive and the plasticizing agent. Plasticizer compatibility with the adhesive can also be dependent upon the chemical nature of the plasticizer and the monomeric content of the adhesive.

Useful plasticizing agents include polyalkylene oxides having weight average molecular weights of 150 to 5,000, or 150 to 1,500, such as polyethylene oxides, polypropylene oxides, polyethylene glycols, and copolymers thereof; alkyl or aryl functionalized polyalkylene oxides, such as PYCAL™ 94 (a phenyl ether of polyethylene oxide, commercially available from ICI Chemicals); benzoyl functionalized polyethers, such as Benzoflex™ 400 (polypropylene glycol dibenzoate, commercially available from Velsicol Chemicals); monomethyl ethers of polyethylene oxides, Ucon™ 50-HB-400 (polyethylene propylene glycol butyl ethers, commercially available from Dow Chemical) and mixtures thereof. Examples of other useful plasticizing agents include Carbowax™ MPEG 550, a methoxypolyethylene glycol plasticizer having a molecular weight of approximately 550 and available from Union Carbide Corp.; Polyol PPG™ 1025, a polypropylene glycol plasticizer having a molecular weight of approximately 1025 and available from Lyondell Chemical Worldwide, Inc.; Polyol™ PPG 425, a polypropylene glycol plasticizer having a molecular weight of approximately 425 and available from Lyondell Chemical Worldwide, Inc.; and Pluronic™ 25R4, an ethylene oxide/propylene oxide block copolymer plasticizer available from BASF Company.

For aqueous adhesive or pre-adhesive compositions, hydrophilic plasticizers are preferred. Nonlimiting examples of plasticizers include monohydric alcohols (e.g., ethanol and isopropanol), polyhydric alcohols, (e.g., ethylene glycol, propylene glycol, polyethylene glycol (molecular weight between 200 and 600) and glycerin, ether alcohols, hydroxyalkylamines, such as triethanolamine and alkyl amines such as triethyl amine.

For non-aqueous compositions oil soluble species such as phthalates (e.g. dioctyl adipate, and bis 2-ethylhexyl adipate), citrates (e.g. trihexyl citrate and trioctyl citrate), adipates (e.g. dioctyl phthalate, and bis 2-ethylhexyl phthalate) and maleates (e.g. dibutyl maleate).

The (meth)acrylate copolymer may be prepared by an emulsion polymerization process. In emulsion polymerization a reaction occurs in micelles or emulsion microdrops suspended in aqueous medium. Any heat generated in the microdrops or micelles is quickly moderated by the effect of the heat capacity of the surrounding water phase. Emulsion polymerization proceeds with better control of exothermic reactions, and the resulting adhesive composition is nonflammable as the aqueous medium is the dominant component.

The pressure sensitive adhesives of the present invention are prepared by a batch, continuous or semi-continuous emulsion polymerization process. The polymerization generally comprises the steps of:
(a) making a monomer premix comprising
 (i) a (meth)acrylic acid ester monomer,
 (ii) an acid functional monomer;
 (iii) optionally a polar monomer,
 (iv) optionally a vinyl monomer,
 (v) optionally a multifunctional (meth)acrylate;
 (vi) optionally a chain transfer agent,
(b) combining said premix with a water phase comprising
 (i) water,
 (ii) a surfactant selected from the group consisting of anionic surfactants, nonionic surfactants, cationic surfactants, amphoteric surfactants, polymeric surfactants, and mixtures thereof,
 (iii) a free radical initiator, preferable a water soluble initiator,
(c) concurrently agitating and heating said emulsion to a temperature of about 30° C. to about 80° C., and permitting polymerization of said monomers in the oil-in-water emulsion until a polymeric latex is formed. It will be understood that other mixtures may be used. For example, the acid functional monomer, or other hydrophilic monomers, may be added to the aqueous solution. In addition, once the emulsion mixture is prepared, the monomers may partition between the oil phase and the water phase, according to their respective partition coefficients.

In the semicontinuous process, a flask is charged with a seed monomer mixture comprising deionized (DI) water, surfactant, acid functional monomers, (meth)acrylate ester monomers, optional co-polymerizable monomers, including optional polar monomers, vinyl monomer, and any optional chain transfer agents, pH modifiers or other additives. The mixture is stirred and heated under an inert atmosphere such as a nitrogen blanket. When the mixture has reached induction temperature, typically about 50° to about 70° C., the first initiator is added to initiate the polymerization and the reaction is allowed to exotherm. After the seed reaction is completed, the batch temperature is then raised to the feed reaction temperature, about 70° to about 85° C. At the feed reaction temperature, the monomer pre-emulsion comprising deionized water, surfactant acid functional monomers, (meth) acrylate ester monomers, optional co-polymerizable monomers, including optional polar monomers, chain transfer agents or other additives is added to the stirred flask over a period of time, typically 2 to 4 hours, while the temperature is maintained. At end of the feed reaction, the second initiator charge, if used, is added to the reaction to further reduce residual monomers in the emulsion. After an additional hour of heating, the mixture is cooled to room temperature (about 23° C.) and the emulsion is collected for evaluation.

The pH of the emulsion is initially acidic. A neutralizing agent may be employed in the preparation of this copolymer. It may be employed at a level sufficient to neutralize all or a part of the acid groups of the polymer. Neutralization is achieved via the use of an alkali metal hydroxide or a combination of an alkali metal hydroxide with a minor amount of another neutralizing agent. A wide variety of other neutralizing agents or buffer solutions (e.g., sodium bicarbonate and the like) may be used as will be understood by those skilled in the art. The selection of the other neutralizing agent, and the amount employed may be varied to the desired pH levels. However, the type and amount selected must not render the adhesive non-dispersible. Preferably ammonium, sodium and potassium hydroxide are used as neutralizing agents.

An alternate method of preparing a pressure sensitive adhesive article comprises partially polymerizing monomers to produce a syrup polymer comprising the acid functional (meth)acrylate copolymer and unpolymerized monomers. Generally, the aziridine crosslinking agent is added to the partially polymerized composition, then coated on a suitable substrate and further polymerized. The syrup polymer composition is polymerized to a useful coating viscosity, which may be coated onto a substrate (such as a tape backing) and further polymerized. Partial polymerization provides a coatable solution of the acid functional (meth)acrylate solute copolymer in one or more solvent monomers.

For syrup application processing, a preferred monomer mixture (second component) comprises 85 to 99 pbw of one or more (meth)acrylate ester monomers, 1 to 15 pbw of acid functional monomers, 0 to 10 pbw of one or more second, non-acid, polar monomers, and 0 to about 5 pbw of other vinyl monomers, based on 100 parts total monomer.

The polymerizations may be conducted in the presence of, or preferably in the absence of, suitable solvents such as ethyl acetate, toluene and tetrahydrofuran which are unreactive with the functional groups of the components of the syrup polymer.

Polymerization can be accomplished by exposing the syrup polymer composition to energy in the presence of a photoinitiator. Energy activated initiators may be unnecessary where, for example, ionizing radiation is used to initiate polymerization. These photoinitiators can be employed in concentrations ranging from about 0.0001 to about 3.0 pbw, preferably from about 0.001 to about 1.0 pbw, and more preferably from about 0.005 to about 0.5 pbw, per 100 pbw of the third component solvent monomer.

A preferred method of preparation of the coatable syrup polymer is photoinitiated free radical polymerization. Advantages of the photopolymerization method are that 1) heating the monomer solution is unnecessary and 2) photoinitiation is stopped completely when the activating light source is turned off. Polymerization to achieve a coatable viscosity may be conducted such that the conversion of monomers to polymer is up to about 30%. Polymerization can be terminated when the desired conversion and viscosity have been achieved by removing the light source and by bubbling air (oxygen) into the solution to quench propagating free radicals. The solute polymer(s) may be prepared conventionally in a non-monomeric solvent and advanced to high conversion (degree of polymerization). When solvent (monomeric or non-monomeric) is used, the solvent may be removed (for example by vacuum distillation) either before or after formation of the syrup polymer. While an acceptable method, this procedure involving a highly converted functional polymer is not preferred because an additional solvent removal step is required, another material may be required (the non-monomeric solvent), and dissolution of the high molecular weight, highly converted solute polymer in the monomer mixture may require a significant period of time.

Useful photoinitiators include benzoin ethers such as benzoin methyl ether and benzoin isopropyl ether; substituted acetophenones such as 2,2-dimethoxyacetophenone, available as Irgacure™ 651 photoinitiator (Ciba-Geigy Corp.; Ardsley, N.Y.), 2,2dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalenesulfonyl chloride; and photoactive oximes such as 1-phenyl-1,2-propanedione-2-(O-ethoxy-carbonyl)oxime. Particularly preferred among these are the substituted acetophenones.

Preferred photoinitiators are photoactive compounds that undergo a Norrish I cleavage to generate free radicals that can initiate by addition to the acrylic double bonds. The photoinitiator can be added to the mixture to be coated after the copolymer has been formed, i.e., photoinitiator can be added to the syrup polymer mixture. Such polymerizable photoinitiators are described, for example, in U.S. Pat. Nos. 5,902,836 and 5,506,279 (Gaddam et al.).

The syrup polymer composition and the photoinitiator may be irradiated with activating UV radiation to polymerize the monomer component(s). UV light sources can be of two types: 1) relatively low light intensity sources such as backlights which provide generally 10 mW/cm$^2$ or less (as measured in accordance with procedures approved by the United States National Institute of Standards and Technology as, for example, with a Uvimap™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially polymerize the syrup polymer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$. Such photoinitiators preferably are present in an amount of from 0.1 to 1.0 pbw per 100 pbw of the syrup polymer composition.

Accordingly, relatively thick coatings (e.g., at least about 1 mil or 25.4 micrometers) can be achieved when the extinction coefficient of the photoinitiator is low.

The degree of conversion can be monitored during the irradiation by measuring the index of refraction of the polymerizing medium as previously described. Useful coating viscosities are achieved with conversions (i.e. the percentage of available monomer polymerized) in the range of up to 30%, preferably 2-20%, more preferably from 5-15%, and most preferably from 7-12%. The molecular weight (weight average) of the solute polymer(s) is at least 100,000, preferably at least 500,000.

When preparing pressure sensitive adhesives, it is expedient for the photoinitiated polymerization reactions to proceed to virtual completion, i.e., depletion of the monomeric components, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds extraneous material that will remain with the system and inhibit the desired polymerization of the syrup polymer and formation of the crosslinked pressure sensitive adhesives of the invention. Free radical polymerization inhibitors are often required at processing temperatures of 70° C. and higher for reaction periods of more than about 6 to 10 hours.

In some embodiments, the adhesive copolymers may be prepared by solution methods. A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and an ethylene glycol alkyl ether. These solvents can be used alone or as mixtures thereof.

With respect to emulsion copolymers, it is beneficial to blend the aziridine crosslinking agents under conditions of low shear, such as by hand-blending. It has been found that such low shear blending beneficially affects the ultimate shear properties of the coated adhesives. It is further beneficial to allow sufficient dwell time to allow the adhesive copolymer and aziridine crosslinking agent to react prior to coating.

In other embodiments, such as with solution copolymers, it is preferable to coat the adhesive composition soon after preparation. The adhesive polymer composition, (containing the copolymer, monomers and aziridine crosslinking agent), either as a syrup or solution are easily coated upon suitable flexible backing materials by conventional coating techniques, then further polymerized, and cured or dried, to produce adhesive coated sheet materials. When emulsion polymerization techniques are used, an emulsion comprising the extant copolymer, aziridine crosslinking agent is coated and dried (preferably after a suitable dwell time) to produce adhesive coated sheet materials. The flexible backing material may be any material conventionally utilized as a tape backing, optical film or any other flexible material.

Examples of materials that can be included in the flexible support include polyolefins such as polyethylene, polypropylene (including isotactic polypropylene), polystyrene, polyester, polyvinyl alcohol, poly(ethylene terephthalate), poly (butylene terephthalate), poly(caprolactam), poly(vinylidene fluoride), polylactides, cellulose acetate, and ethyl cellulose and the like. Commercially available backing materials useful in the invention include kraft paper (available from Monadnock Paper, Inc.); cellophane (available from Flexel Corp.); spun-bond poly(ethylene) and poly(propylene), such as Tyvek™ and Typar™ (available from DuPont, Inc.); and porous films obtained from poly(ethylene) and poly(propylene), such as Teslin™ (available from PPG Industries, Inc.), and Cellguard™ (available from Hoechst-Celanese).

Backings may also be prepared of fabric such as woven fabric formed of threads of synthetic or natural materials such as cotton, nylon, rayon, glass, ceramic materials, and the like or nonwoven fabric such as air laid webs of natural or synthetic fibers or blends of these. The backing may also be formed of metal, metallized polymer films, or ceramic sheet materials may take the form of any article conventionally known to be utilized with pressure sensitive adhesive compositions such as labels, tapes, signs, covers, marking indicia, and the like.

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating knife coating, and die coating. These various methods of coating allow the compositions to be placed on the substrate at variable thicknesses thus allowing a wider range of use of the compositions. Coating thicknesses may vary as previously described. The solutions may be of any desirable concentration, and degree of conversion, for subsequent coating, but is typically between 20 to 70 wt. % polymer solids, and more typically between 30 and 50 wt. % solids, in solvent. The emulsions also may be of any desirable concentration for subsequent coating, but is typically between 30 to 70 wt. % polymer solids, and generally contains less than 2% unreacted monomer. The syrup polymers may be of any desirable concentration for subsequent coating, but is typically between 5 to 20 wt. % polymer solids in monomer. The desired concentration may be achieved by further dilution of the coating composition, or by partial drying.

The flexible support may also comprise a release-coated substrate. Such substrates are typically employed when an adhesive transfer tape is provided. Examples of release-coated substrates are well known in the art and include, by way of example, silicone-coated kraft paper and the like. Tapes of the invention may also incorporate a low adhesion backsize (LAB) which are known in the art.

In some embodiments, such as with syrup copolymers, the syrup may be coated and cured using a construction which comprises a layer of syrup copolymer coated between two liners at least one of which is coated with a release material. The release liners typically comprise a clear polymeric material such as polyester that is transparent to ultraviolet radiation. Preferably, each release liner is first coated or primed with a release material which is incompatible with the acrylate adhesive copolymer. The adhesive composition may be cured by exposure to ultraviolet radiation which is transmitted through the release liner(s).

EXAMPLES

Test Methods

Peel Adhesion Test [ASTM D 3330/D 3330M-04]

Two 0.5 inch by at least 4 inch (~1.3×10 cm) strips of adhesive coated onto polypropylene film (for emulsion copolymers) or Mitsubishi Hostphan™ primed polyester film (for solution copolymers) were adhered to a glass plate by rolling a 2 kg roller onto the tape. At least 3.5 lineal inches (~8.9 cm) of the adhesive coated film sample was in contact with the glass plate and a short portion of the sample (the "free end") was kept from contacting the glass plate. The free end of the sample was pulled back to form a nearly 180° angle with the portion of the sample that was adhered to the glass plate. The free end of the sample was attached to the clamp of the adhesion tester scale. The peel adhesion test was initiated as soon as the sample was adhered to the glass plate, that is, the "dwell time" was kept as close to zero as possible. The force required to peel the tape was measured in ounces per 0.5 inches width with a platen speed of 90 inches per minute. The measurements for the two tape samples were averaged. Peel adhesion data was then normalized to Newtons/decimeter (N/dm) for the tables below.

Shear Strength Test [ASTM D-3654/D 3654M 06, PSTC-7]

For shear testing, a 0.5 inch by at least 4 inch (~1.3×10 cm) strip of adhesive coated onto polypropylene film was adhered by its adhesive to a substrate (fiberboard for emulsion copolymers and stainless steel for solution copolymers) and cut down to leave a 0.5 inch by 0.5 inch square (~1.3×1.3 cm) of adhesive coated sample adhered to the substrate with several inches of the free end of the sample looped back upon itself to form a loop for attaching a weighted load. A weight of 2 kg was rolled over the adhered portion. The tape sample was hung in a 70° C. oven (for 70° C. shear testing) or in a constant temperature and humidity (CT) room (for room temperature shear testing). A 1000 g load was attached to the tape sample for testing. The shear strength test was initiated as soon as the sample was adhered to the substrate, that is, the "dwell time" was kept as close to zero as possible. Each sample was suspended until failure and/or test terminated. The time, in minutes, for the sample to separate from the substrate was recorded as the shear strength. The time to failure, as well as the mode of failure, were recorded. Samples were run in triplicate and averaged for the tables below.

Shear Stress Relaxation Test

A 1×4 inch (~2.5×10 cm) strip of the tape was adhered by its adhesive to a stainless steel panel and cut down to leave a 1×1 square inch (2.5×2.5 cm) of adhesive coated sample adhered to the substrate, leaving about 2 inches at the free end. A weight of 2 kg was rolled over the adhered portion. The sample was mounted vertically to a TA-XT PLUS™ Texture Analyzer (Stable Micro Systems Ltd., UK) by firmly holding the stainless steel panel and the free end of the adhesive strip with two metal grips respectively. The bottom grip was attached to the base of the instrument and the upper grip was attached to the movable arm. The upper grip was initially moved up at 2 mm/sec to apply a shear force of 4 kg to the adhesive bond. Then its position was fixed, and the stress decay was monitored over a time span of 2 minutes. The shear-stress relaxation was calculated as (1-final force/4 kg)× 100%. Samples were run in triplicate and averaged for the tables below. Less stress relaxation is an indication of a stronger polymer network.

| Materials | |
|---|---|
| Raw Materials | Sources |
| Isooctyl acrylate (IOA) | 3M St. Paul MN |
| Acrylic Acid (AA) | Alfa Aesar, Wardhill, MA |
| Isopthaloyl dichloride | Aldrich Chemical, Milwaukee, WI |
| 2-Methylaziridine 90% | Aldrich Chemical, Milwaukee, WI |
| 1,10-Decanediol | Alfa Aesar, Wardhill, MA |
| Poly(propylene glycol) | Aldrich Chemical, Milwaukee, WI |
| Hydrogenated hydroxyl terminated polyolefin. | Sartomer Company, Inc. Exton, PA |
| Poly(ethylene glycol) 1000 (PEG 1000) | Lancaster Synthesis Ltd., Windham, NH |
| Phthalic anhydride | Aldrich Chemical, Milwaukee, WI |
| Oxalyl chloride | Alfa Aesar, Wardhill, MA |
| Bisamide. 5.0 wt % in toluene. | 1,1'-isophthaloyl-bis-1-methylaziridine, C.A.S. 7652-64-4 |
| Adhesive 1 Isooctyl acrylate/acrylic acid (90/10). inherent viscosity of 0.48 dL/g at 0.5 g/dL, Solid: 45.2%. | Prepared as described in U.S. Re 24906 (Ulrich) |
| Adhesive 2 Isooctyl acrylate/acrylic acid (90/10). inherent viscosity of 0.72 dL/g at 0.5 g/dL. Solid: 41.2% in heptane (67%)/acetone (33%) | Prepared as described in U.S. Re 24906 (Ulrich) |

Preparative Example 1

Synthesis of 1,10-decanediol bis(3-(2-methyl-aziridine-1-carbonyl)-benzoic acid) ester (Flex-10)

Part A. Synthesis of 1,10-decanediol bis(3-chlorocarbonylbenzoic acid) ester

To a 3 L, three-neck, round bottom flask equipped with a magnetic stirrer, a thermometer, and a bubbler was added isophthaloyl dichloride (1950 g, 9.60 mol). The flask was heated at 55° C. To the flask was added 1,10-decanediol (112 g, 0.64 mol) in portions. After stirring the reaction mixture at 55° C. for 1 hour, the excess isophthaloyl dichloride was removed by vacuum distillation (200 mTorr, 100° C.) and was recycled. A stream of dry nitrogen was bubbled through the mixture while distilling so the isophthaloyl dichloride residue could be removed completely. A white solid (311 g) was obtained as product.

Part B. Synthesis of 1,10-decanediol bis(3-(2-methyl-aziridine-1-carbonyl)-benzoic acid) ester (Flex-10)

To a 3 L, three-neck, round bottom flask equipped with a magnetic stirrer, a thermometer, and an addition funnel were added an aqueous NaOH solution (563 g of a 10.0 weight percent solution), toluene (500 mL), and 2-methylaziridine (89.3 g of 90% pure 2-methylaziridine, 1.41 mol). The mixture was stirred and cooled to −10° C. to −5° C. To this stirred mixture was added 1,10-decanediol bis(3-chlorocarbonylbenzoic acid) ester (311 g) in toluene (500 mL) solution over a period of 30 minutes. When addition was complete, the mixture was stirred at room temperature overnight. The organic phase was then washed with water, dried over magnesium sulfate (MgSO$_4$), filtered and concentrated under vacuum at room temperature to give 331.5 g of 1,10-decanediol bis(3-(2-methylaziridine-1-carbonyl)benzoic acid) ester (Flex-10) as a pale yellow oil

Preparative Example 2

Synthesis of poly(propylene glycol) bis(3-(2-methyl-aziridine-1-carbonyl)benzoic acid) ester (Flex-50)

Part A. Synthesis of poly(propylene glycol) bis(3-chlorocarbonylbenzoic acid) ester To a 1 L, three-neck, round bottom flask equipped with a magnetic stirrer, a thermometer, and an adapter was added isophthaloyl dichloride (223 g, 1.10 mol). The flask was heated at 65° C. To the flask was added poly(propylene glycol) (mw=~1000) (57.9 g, 57.9 mmol) in portions. After stirring the reaction mixture at 55° C. for 2 hours, the excess isophthaloyl dichloride was removed by vacuum distillation (200 mTorr, 100° C.) and was recycled. A stream of dry nitrogen was bubbled through the mixture while distilling so the isopthaloyl dichloride residue could be removed completely. A pale yellow liquid (76.5 g) was obtained as product.

Part B. Synthesis of poly(propylene glycol) bis(3-(2-methyl-aziridine-1-carbonyl)benzoic acid) ester (Flex-50)

To a 2 L, three-neck, round bottom flask equipped with a magnetic stirrer, a thermometer, and an addition funnel were added an aqueous NaOH solution (510 g of a 10.0 weight percent solution), methylene chloride (100 mL), and 2-methylaziridine (13.2 g). The mixture was stirred and cooled to −10° C. to −5° C. To this mixture was added poly(propylene glycol) bis-(3-chlorocarbonylbenzoic acid) ester (76.5 g) in 100 mL of methylene chloride ($CH_2Cl_2$) solution over a 15 minute period. When addition was complete, the mixture was stirred at room temperature overnight. The organic phase was washed with water, dried over $MgSO_4$, filtered and concentrated under vacuum at room temperature to give 72.7 g of poly(propylene glycol) bis(3-(2-methyl-aziridine-1-carbonyl)benzoic acid) ester (Flex-50) as a pale yellow oil.

Preparative Example 3

Synthesis of 3-(2-Methyl-aziridine-1-carbonyl)-benzoic acid ester terminated hydrogenated polyolefin (Flex-180)

Part A. Synthesis of 3-chlorocarbonylbenzoic acid ester terminated hydrogenated polyolefin To a 1 L, three-neck, round bottom flask equipped with a magnetic stirrer, a thermometer, and an adapter was added isophthaloyl dichloride (406 g, 2.0 mol). The flask was heated at 55° C. To the flask was added hydrogenated hydroxyl terminated polyolefin (Sartomer Company, Inc., Krasol HLBH-P 2000™, 383 g) in portions. After stirring at 55° C. for 1 hour, the excess isophthaloyl dichloride was removed by vacuum distillation (200 mTorr, 100° C.) and was recycled. A stream of dry nitrogen was bubbled through the mixture while distilling so the isophthaloyl dichloride residue could be removed completely. A pale yellow liquid (404 g) was obtained as product.

Part B. Synthesis of 3-(2-methylaziridine-1-carbonyl)benzoic acid ester terminated hydrogenated polyolefin (Flex-180)

To a 1 L, three-neck, round bottom flask equipped with a magnetic stirrer, a thermometer, and an addition funnel was added an aqueous NaOH solution (24.0 g of a 10.0 weight percent solution), $CH_2Cl_2$ (200 mL), and 2-methylaziridine (3.7 g of 90% 2-methylaziridine, 0.06 mol). The mixture was stirred and cooled to −10° C. to −5° C. To this mixture was added 3-chlorocarbonylbenzoic acid ester terminated hydrogenated polyolefin in $CH_2Cl_2$ (200 mL) solution over a 60 minute period. The mixture was then stirred at room temperature overnight. The organic phase was isolated by centrifugation. It was washed with water, dried over $MgSO_4$, filtered and concentrated under vacuum at room temperature to give 42.0 g of 3-(2-methylaziridine-1-carbonyl)benzoic acid ester terminated hydrogenated polyolefin (Flex-180) as a colorless oil.

Preparative Example 4

Synthesis of poly(ethylene glycol)1000 bis(3-(2-methylaziridine-1-carbonyl)benzoic acid) ester (Flex-70)

Part A. Synthesis of poly(ethylene glycol)1000 bis(3-chlorocarbonylbenzoic acid) ester To a 1 L, three-neck, round bottom flask equipped with a magnetic stirrer, a thermometer, and an adapter was added isophthaloyl dichloride (812 g, 4.0 mol). The flask was heated at 100° C. To the flask was added poly(ethylene glycol)1000 (158 g, 0.16 mol) in portions. After stirring the reaction mixture at 100° C. for 1 hour, the excess of isophthaloyl dichloride was removed by vacuum distillation (200 mTorr, 100° C.) and was recycled. A stream of dry nitrogen was bubbled through the mixture while distilling so the isophthaloyl dichloride residue could be removed completely. A pale yellow liquid (210 g) was obtained as product.

Part B. Synthesis of poly(ethylene glycol)1000 bis (3-(2-methylaziridine-1-carbonyl)benzoic acid) ester (Flex-70)

To a 1 L, three-neck, round bottom flask equipped with a magnetic stirrer, a thermometer, and an addition funnel were added 2-methylaziridine (22.0 g of 90% pure 2-methylaziridne, 0.35 mol), triethylamine (35.1 g, 0.35 mol), and $CH_2Cl_2$ (250 mL). The mixture was stirred and cooled to −10° C. To this solution was added a solution of poly(ethylene glycol) 1000 bis(3-chlorocarbonylbenzoic acid) ester (210 g) in $CH_2Cl_2$ (250 mL) over a period of 60 minutes The mixture was allowed to stir at room temperature for 1 hour, then the white precipitate was removed by filtration. The filtrate was concentrated under high vacuum at RT to give 203 g of (poly(ethylene glycol)1000 bis(3-(2-methylaziridine-1-carbonyl)benzoic acid) ester (Flex-70) as a pale yellow liquid

Preparative Example 5

Synthesis of 1,10-decanediol bis(2-(2-methylaziridine-1-carbonyl)benzoic acid) ester (α-Flex-10)

Part A. Synthesis of 1,10-decanediol bis(2-chlorocarbonylbenzoic acid) ester

To a 1 L, three-neck, round bottom flask equipped with a magnetic stirrer, a condenser, and an adapter was added phthalic anhydride (recrystallized from toluene, 29.6 g, 0.20 mol), 1,10-decanediol (17.4 g, 0.10 mol), and toluene (100 mL). The mixture was stirred and heated at 100° C. overnight and then cooled to 60° C. To this solution was added oxalyl chloride (25.4 g, 0.20 mol) in portions. Bubbles formed immediately following the addition. After heating at 60° C. overnight, the mixture was concentrated under vacuum to give 49.6 g of a colorless liquid.

Part B. Synthesis of 1,10-decanediol bis(2-(2-methylaziridine-1-carbonyl)benzoic acid) ester (α-Flex-10)

To a 1 L, three-neck, round bottom flask equipped with a magnetic stirrer, a thermometer, and an addition funnel were added an aqueous NaOH solution (84.0 g of a 10.0 weight percent solution), toluene (200 mL), and 2-methylaziridine (13.4 g of 90% pure 2-methylaziridine, 0.21 mol). The mixture was stirred and cooled to −10° C. To this mixture was added a solution of 1,10-decandiol bis(2-chlorocarbonyl benzoic acid) ester from Part A (48.6 g) in toluene (150 mL) over a period of 30 minutes. The mixture was then stirred at room temperature overnight. The organic phase was washed with water, dried over MgSO₄, filtered and concentrated under vacuum at room temperature to give 45.6 g 1,10-decanediol bis(2-(2-methylaziridine-1-carbonyl)benzoic acid) ester (α-Flex-10) as a colorless oil.

Preparative Example 6

Comparative 1,10-bis-(2-methylaziridinyl)-hexane-1,10-dione (SEBA)

To a 500 mL round bottom flask equipped with a magnetic stirrer and cooled in an ice-salt bath (−10 to −5° C.), was added an aqueous NaOH solution (66.2 g of a 13.9 weight percent solution), methylene chloride (172 mL), and 2-methylaziridine (14.6 g of 90% pure 2-methylaziridine, 0.23 mol). To this mixture was added sebacoyl chloride (25.0 g, 0.104 mol) dropwise over a period of 15 minutes. The mixture was then stirred at −5° C. for another 60 minutes. Saturated aqueous sodium chloride (100 mL) was added, then the organic phase was collected and washed again with saturated aqueous sodium chloride (200 mL) The organic phase was dried over MgSO₄, filtered, and concentrated under vacuum. The excess starting material was removed by distillation under high vacuum at 20° C. to give 26.0 g (0.093 mol) of the product as a yellow oil.

Preparative Example 7

Reaction product of 1,1'-isophthaloyl-bis-1-methylaziridine and sebacic acid

Sebacic acid (0.207 g), methyl ethyl ketone (MEK, 4.0 g), and 1,1'-isophthaloyl-bis-1-methylaziridine (Bisamide, 10.0 g, 5.0 wt %) toluene solution were mixed at room temperature. The mixture was stirred at 90° C. for 24 hours. The crude reaction mixture, comprising the above-depicted product, higher oligomers, and excess starting materials, was directly compounded with the acrylic copolymer.

Preparative Example 8

Comparative

N,N'-(hexane-1,6-diyl)bis-(2-methylaziridine-1-carboxamide) (HUMBA)

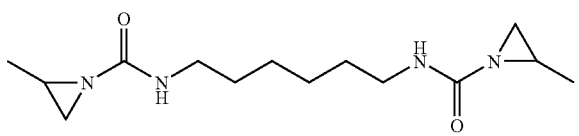

To a stirred solution of (25.2 g, 0.15 mol) in methylene chloride (50 mL) at 0° C. was added dropwise a solution of 2-methylaziridine (20.9 g of 90% pure 2-methylaziridine, 0.33 mol) in methylene chloride (25 mL). When addition was complete, the reaction mixture was allowed to warm to room temperature and was stirred overnight. Solvent and excess 2-methylaziridine were removed at reduced pressure to leave 34.2 g of the product as a colorless oil.

Example 1

Reactivity Comparison

The crosslinkers reactivity in adhesive polymers was evaluated by measuring the viscosities of the formulated mixtures with a Brookfield Engineering Viscometer (Model: LVDVII+, Brookfield Eng. Labs. Inc. Stoughton, Mass. 02072). A spindle 4 was used and the spin speed was 30 RPM. The copolymer used was an IOA/AA polymer solution (Adhesive 2, IOA/AA (90/10 by weight); IV: 0.72; solids: 41.2 wt %; solvent: heptane (67%)/acetone (33%)). Bisamide (5.0 wt % in toluene, 3M) was used as a control. Two aliphatic crosslinked SEBA (preparative example 6) and HUMBA (preparative example 8) were used for comparison. Flex-10, Flex-70, and α-Flex-10 were dissolved in toluene at concentrations of 11.2 wt %, 40 wt %, and 15.0 wt % respectively.

The crosslinkers to be evaluated were added to the IOA/AA polymer solution at the following parts per hundred (phr)

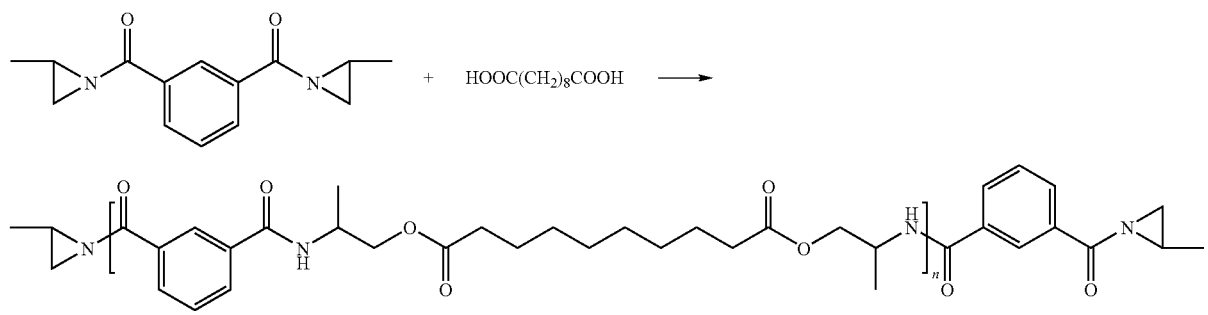

levels based on dry resin: Bisamide, 0.20 phr; SEBA, 0.23 phr; HUMBA, 0.23 phr; Flex-10, 0.45 phr; Flex-70, 1.12 phr; α-Flex-10, 0.45 phr. At these levels, all of the crosslinkers to be evaluated were present in the respective IOA/AA polymer solutions at the same molar concentration. After mixing for 5 minutes, the viscosities of the mixtures were monitored at room temperature over time until a viscosity of 10,000 centipoise (cP) was reached. Table 1 shows the time required for the various adhesive solutions to attain a viscosity of 10,000 cP.

As can be seen from the data in Table 1, the time required for the adhesive compositions containing the aromatic flexible crosslinkers to attain a viscosity of 10,000 cP is greater than the time required for the adhesive composition containing the Bisamide or aliphatic crosslinkers to attain this viscosity. This shows that the stability of the adhesive compositions containing the new aromatic flexible crosslinkers is greater than that of the adhesive composition containing the Bisamide crosslinker or the aliphatic crosslinkers and that the adhesive compositions containing the new aromatic flexible crosslinkers have greater shelf life than the adhesive compositions containing the Bisamide crosslinker or aliphatic crosslinkers.

TABLE 1

Shelf life comparison of the crosslinkers

|  | Bisamide | SEBA Prep Ex. 7 | Prep Ex. 6 | HUMBA Prep Ex. 8 | Flex-10 Prep Ex. 1 | Flex-70 Prep Ex. 4 | α-Flex-10 Prep Ex. 5 |
|---|---|---|---|---|---|---|---|
| Crosslinker concentration (phr) | 0.20 | 0.42 | 0.23 | 0.23 | 0.45 | 1.12 | 0.45 |
| Time required to reach viscosity of 10,000 cP (minutes) | 100 | 146 | 12 | <5 | 153 | 156 | 122 |

Examples 2-5 and Comparative C1

A low molecule weight copolymer (Adhesive 1, IOA/AA 90/10, 45.0 wt % in ethyl acetate; inherent viscosity of 0.48 dL/g at 0.5 g/dL) was used to evaluate the property of the flexible crosslinkers. Bisamide was used as a comparison and was added to the IOA/AA polymer at a concentration of 0.125 parts per hundred (phr). The concentrations of the other crosslinkers in IOA/AA polymer solutions were adjusted according to their molecule weights so that their respective molar concentrations were the same as that of the Bisamide. Therefore, the concentrations of Flex-10, Flex-50, Flex-70, Flex-180 and a Flex-10 were 0.281, 0.701, 0.703, 1.228, and 0.281 phr respectively. The adhesive polymer solution was mixed with crosslinker solution. The formulations were then coated on Mitsubishi Hostphan™ primed polyester film at a 1 mil (~25 micrometers) thickness. The resulting tapes were cured first at 70° C. for 5 minutes then at 110° C. for 3 more minutes. The tapes were left in a constant temperature room (23° C. at 50% relative humidity) for 24 hours before testing. Peel and shear testing were carried according to ASTM D 3330/D 3330M-04 and ASTM D-3654/D 3654M 06, PSTC-7 described previously. The results are summarized in Table 2. In Table 2, "c" stands for cohesive failure; "p" stands for pop off failure; "c/p" stands for a mixture failure mode of cohesive and pop off.

TABLE 2

| Example | Cross-linkers | Peel (90 inch/min) on Glass (N/dm) | Shear Strength on SS (min) RT | 70° C. |
|---|---|---|---|---|
| C1 | Bisamide | 80 | 184 (c) | 1 (c) |
| 2 | Flex-10 | 68 | 2695 (p) | 208 (p) |
| 3 | Flex-50 | 82 | 1445 (p) | 56 (c/p) |
| 4 | Flex-180 | 68 | 1839 (p) | 22 (p) |
| 5 | α-Flex-10 | 77 | 1733 (c/p) | 33 (p) |

Examples 6-9 and Comparative C2

A higher molecule weight polymer (Adhesive 2) was also used to evaluate the properties of the flexible crosslinkers. Bisamide was used as a comparison and was added to the IOA/AA polymer at a concentration of 0.075 parts per hundred (phr). The concentrations of the other crosslinkers in IOA/AA polymer solutions were adjusted according to their molecular weights so that their respective molar concentrations were the same as that of the Bisamide. Therefore, the concentrations of Flex-10, Flex-50, Flex-70, Flex-180 and α-Flex-10 were 0.168, 0.421, 0.422, 0.737, and 0.168 phr respectively. The adhesive polymer solution was mixed with crosslinker solution. The formulations were then coated on Mitsubishi Hostphan™ primed polyester film at a 1 mil (~25 micrometers) thickness. The tapes were cured first at 70° C. for 5 minutes then at 110° C. for 3 more minutes. The tapes were left in a constant temperature room for 24 hours before testing. Peel and shear testing were as described previously. The results are summarized in Table 3. In Table 3, "c" stands for cohesive failure; "p" stands for pop off failure; "c/p" stands for a mixture failure mode of cohesive and pop off.

TABLE 3

| Example | Cross-linkers | Peel (90 in/min) on Glass (N/dm) | Shear Strength on SS (min) (mode of failure) Room temperature | 70° C. |
|---|---|---|---|---|
| C2 | Bisamide | 81 | 10 k+ | 8552 (c) |
| 6 | Flex-10 | 80 | 10 k+ | 100,000+ |
| 7 | Flex-50 | 72 | 10 k+ | 8181 (c/p) |
| 8 | Flex-180 | 67 | 10 k+ | 10,000+ |
| 9 | α-Flex-10 | 72 | 10 k+ | 10,000+ |

Examples 10 and C3

Shear-Stress Relaxation Test

Adhesive 2 was mixed with Flex-10 and Bisamide at a ratio of 0.168 phr and 0.075 phr respectively. The formulations were then coated on Mitsubishi Hostphan™ primed polyester film at a 2 mil (~50 micrometers) thickness. The tapes were cured first at 70° C. for 5 minutes then at 110° C. for 3 more minutes. The tapes were left in a constant temperature room for 24 hours before testing by the Shear Stress Relaxation Test. The results are shown in Table 4. Less stress relaxation is an indication of a stronger polymer network. As shown in Table 4, the polymer incorporating Flex-10 is stronger and more efficiently crosslinked.

TABLE 4

Shear-stress relaxation comparison.

| Example | Crosslinkers | Shear-stress relaxation |
|---|---|---|
| C3 | Bisamide | 26.7% |
| 10 | Flex-10 | 21.4% |

Examples 11-18 and C4

Comparison of Flexible Crosslinker with the Bisamide in Low Surface Energy Adhesive Formulation

Part A. Preparation of Adhesive Copolymer

To a bottle were added 48.0 grams of 2-ethyl hexyl acrylate (2-EHA, obtained from Dow Chemical Co.), 4.5 grams of butyl acrylate (BA), 4.5 grams of acrylic acid (AA, obtained from BASF Corp. and 0.200 grams of VAZO-67 (an azonitrile polymerization initiator obtained from DuPont) in a 3:1 ratio of ethyl acetate and toluene. This mixture was purged with nitrogen to remove all oxygen and the bottle was then sealed. This sealed bottle was placed in a water bath and heated at 58° C. for 24 hours. The resulting sample was further diluted with an additional 56 grams of ethyl acetate. The final sample was a clear, viscous solution. The percent solids was 43.2 and the intrinsic viscosity was 1.13.

Part B

Bisamide (at a concentration of 0.1 wt % based on dry resin) was used as a control. Flexible crosslinkers Flex-10 and Flex-50 were tested at four concentrations so they were equivalent to 0.05%, 0.075%, 0.1% and 0.125% of Bisamide. All ingredients, including adhesive copolymer solution and tackifiers and excepting crosslinkers, were added into a glass jar. Toluene was added to make solution of 35% solids. The jar was put on a roller overnight for mixing. The respective crosslinkers were added into the jar right before coating. The detailed compositions are listed in Table 5. The adhesive solution was coated on polyethylene terephthalate (PET) film backing using a 6" knife coater. The coater gap was set to give 2.0 mil thick adhesive after drying. The sample was dried in an oven at 70° C. for 10-15 minutes, covered with a release liner and stored in a constant temperature room before testing. The tapes were cut to 0.5" (~12.5 cm) wide and laminated onto polypropylene substrate. After dwelling a specific time (15 min and 24 hours), peel forces were measured at 90° peeling angle at a speed of 12"/minute (~25 cm/minute). Shear strength were measured using stainless steel substrates at both room temperature and at 70° C.

TABLE 5

Adhesion comparison on low surface energy substrate

| Example | Crosslinker (phr) | RT Shear (min) | 70° C. Shear (min) | 90° Peel on PP (Dwell time 15 min) (N/dm) | 90° Peel on PP (Dwell time 24 hours) (N/dm) |
|---|---|---|---|---|---|
| C4 | Bisamide (0.100) | 8000+ | 391 | 95 | 108 |
| 11 | Flex-10 (0.112) | 5706 | 1274 | 90 | 122 |
| 12 | Flex-10 (0.169) | 2615 | 4175 | 97 | 111 |
| 13 | Flex-10 (0.225) | 2298 | 920 | 101 | 114 |
| 14 | Flex-10 (0.281) | 2736 | 442 | 91 | 99 |
| 15 | Flex-50 (0.281) | 1785 | 110 | 107 | 117 |
| 16 | Flex-50 (0.421) | 3961 | 1642 | 103 | 124 |
| 17 | Flex-50 (0.561) | 3089 | 3005 | 90 | 115 |
| 18 | Flex-50 (0.702) | 2954 | 7660 | 98 | 104 |

The invention claimed is:

1. A crosslinking agent of the formula:

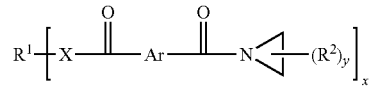

Wherein
  $R^1$ is a polyvalent organic group having a chain length of 2 to 250 atoms;
  X is —O— or —$NR^3$—, where $R^3$ is H or $C_1$-$C_4$ alkyl;
  Ar is a divalent arylene group;
  $R^2$ is H or $C_1$-$C_4$ alkyl;
  x is 2 or 3, and y is 0, 1 or 2.

2. The crosslinking agent of claim 1, where $R^1$ is a polyvalent alkylene of 2 to 250 carbon atoms.

3. The crosslinking agent of claim 1 where $R^1$ is a poly (alkylene oxide) having a chain length of 2 to 250 atoms.

4. The crosslinking agent of claim 1 wherein x is 2.

5. The crosslinking agent of claim 1 wherein Ar is phenylene, napthylene, or anthracene.

6. A crosslinking agent of the formula:

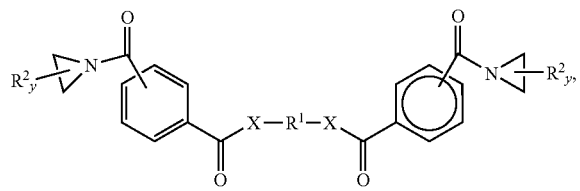

where
  $R^1$ is a polyvalent organic group having a chain length of 2 to 250 atoms;
  X is —O— or —$NR^3$—, where $R^3$ is H or $CH_3$;
  $R^2$ is H or $C_1$-$C_4$ alkyl;
  and y is 0, 1 or 2.

7. A crosslinking agent of the formula:

$$\begin{array}{c} (R^2)_y \\ N \end{array} \!\!\!-\!\!\! \begin{array}{c} O \\ \| \\ C \end{array} \!\!\!-\!\!\! Ar \!\!\!-\!\!\! \begin{array}{c} O \\ \| \\ C \end{array} \!\!\!-\!\!\! NHCH_2\overset{R^2}{\underset{}{C}}H \!\!\!-\!\!\! O \!\!\!-\!\!\! \begin{array}{c} O \\ \| \\ C \end{array} \!\!\!-\!\!\! R^5 \!\!\!-\!\!\! \begin{array}{c} O \\ \| \\ C \end{array} \!\!\!-\!\!\! O \!\!\!-\!\!\! \overset{R^2}{\underset{}{C}}HCH_2 \!\!\!-\!\!\! \overset{H}{\underset{}{N}} \!\!\!-\!\!\!\Big]_b\!\!\!-\!\!\! \begin{array}{c} O \\ \| \\ C \end{array} \!\!\!-\!\!\! Ar \!\!\!-\!\!\! \begin{array}{c} O \\ \| \\ C \end{array} \!\!\!-\!\!\! N\begin{array}{c} (R^2)_y \\ \end{array}$$

wherein
   Ar is a divalent arylene group;
   $R^2$ is H or $C_1$-$C_4$ alkyl;
   b is at least 1;
   y is 0, 1 or 2;
   $R^5$ is selected from divalent $C_1$-$C_{20}$ alkylene, arylene, alkyarylane or poly(alkylene oxide).

8. A crosslinkable composition comprising an acid-functional (meth)acrylate copolymer and the crosslinking agent of claim 1.

9. The crosslinkable composition of claim 8 wherein the acid-functional (meth)acrylate copolymer comprises:
   i. 85 to 99 parts by weight of an (meth)acrylic acid ester of non-tertiary alcohol;
   ii. 1 to 15 parts by weight of an acid functional ethylenically unsaturated monomer;
   iii. 0 to 10 parts by weight of a non-acid functional, ethylenically unsaturated polar monomer;
   iv. 0 to 5 parts vinyl monomer; and
   v. 0 to 5 parts of a multifunctional (meth)acrylate;
   based on 100 parts by weight total monomer.

10. The crosslinkable composition of claim 8 comprising 0.005 to 5.0 parts by weight of the crosslinking agent, relative to 100 parts of the copolymer.

11. The crosslinkable composition of claim 9 wherein said non-acid functional, ethylenically unsaturated monomer is selected from 2-hydroxyethyl (meth)acrylate; N-vinylpyrrolidone; N-vinylcaprolactam; acrylamide; t-butyl acrylamide; dimethylamino ethyl acrylamide; N-octyl acrylamide; poly(alkoxyalkyl) (meth)acrylates; vinyl methyl ether; and mixtures thereof.

12. The crosslinkable composition of claim 8 wherein said copolymer comprises 1 to 5 parts by weight of acrylic acid and 1 to 5 parts by weight of a polar monomer, based on 100 parts by weight total monomer.

13. The crosslinkable composition of claim 8 wherein said composition is an aqueous emulsion.

14. The crosslinkable composition of claim 8 wherein the acid functional monomer is selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropane sulfonic acid, vinyl phosphonic acid, and mixtures thereof.

15. The crosslinkable composition of claim 8 comprising 1 to 5 parts of a vinyl monomer selected from vinyl esters, styrene, substituted styrene, vinyl halide, vinyl propionate, and mixtures thereof, based on 100 parts by weight total monomer.

16. A pressure sensitive adhesive comprising the crosslinked composition of claim 8.

17. An emulsion comprising:
   (a) 30 to about 70 weight percent, based on the total weight of the emulsion, of the crosslinkable composition of claim 8, and
   (b) 30 to 70 weight percent of an aqueous phase comprising a surfactant, based on the total weight of the emulsion.

18. The emulsion of claim 17 wherein said composition has a pH of greater than 7.

19. A syrup polymer composition comprising:
   a) first component solute polymer comprising:
      i. 85 to 99 parts by weight of an (meth)acrylic acid ester of non-tertiary alcohol;
      ii. 1 to 15 parts by weight of an acid functional monomer;
      iii. 0 to 10 parts by weight of a second, non-acid functional, polar monomer;
      iv. 0 to 5 parts vinyl monomer, and
   b) a second component comprising at least one free-radically polymerizable solvent monomer, and
   c) the aziridine crosslinking agent of claim 1.

20. A method of making the crosslinking agent of claim 1 comprising the steps of reacting a diol or diamine having 2 to 250 chain atoms with a bis-acyl aryl compound, and reacting the product thereof with an aziridine compound.

21. The method of claim 20 wherein the diol or diamine is of the formula $R^1(XH)_2$, where
   $R^1$ is a polyvalent organic group having a chain length of 2 to 250 atoms; and X is —O— or —$NR^3$—, where $R^3$ is H or $CH_3$.

22. The method of claim 20 wherein the bis-acyl aryl compound is an aryl anhydride.

* * * * *